(12) United States Patent
Lee-Huang

(10) Patent No.: US 6,652,861 B1
(45) Date of Patent: Nov. 25, 2003

(54) ANTI-HIV AND ANTI-TUMOR PEPTIDES AND TRUNCATED POLYPEPTIDES OF MAP30

(75) Inventor: Sylvia Lee-Huang, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/645,603

(22) Filed: Aug. 25, 2000

Related U.S. Application Data

(60) Provisional application No. 60/150,885, filed on Aug. 26, 1999.

(51) Int. Cl.[7] .................. A61K 39/00; A61K 45/00; A61K 38/00; A61K 35/98; A01N 37/18; A01N 14/00; C07K 17/00; C07K 38/16

(52) U.S. Cl. .................. 424/185.1; 424/277.1; 424/278.1; 514/2; 530/350; 530/370

(58) Field of Search .................. 530/300, 350, 530/379, 370; 514/2; 424/207.1, 185.1, 277.1, 278.1

(56) References Cited

U.S. PATENT DOCUMENTS 5,484,889 A * 1/1996 Lee-Huang et al. ........ 530/379

OTHER PUBLICATIONS

Lee–Huang et al. 1990. MAP 30: a new inhibitor of HIV–1 infection and replication. FEBS vol. 272(12): 12–18.*
Tumer et al. C–terminal deletion mutant of pokeweed antiviral protein inhibits viral infection but does not depurinate host ribosomes. PNAS. vol. 94, pp. 3866–3871.*

Lee–Huang, et al, TAP 29: An anti–human immunodeficiency virus protein from *Trichosanthes kirikowil* that is nontoxic to intact cells, Proc. Natl. Acad. Sci. USA, 1991, 88, 6570–6574.

Lee–Huang, et al., Plant Proteins with Antiviral Activity Against Human Immunodeficiency Virus, Natural Products as Antiviral Agents, 1992, 153–170, Edited by C.K. Chu and H.G. Culter, Plenum Press, New York.

Lee–Huang, et al., Human immunodeficiency virus type 1 (HIV–1) inhibition, DNA–binding, RNA–binding, and ribosome inactivation activities in the N–terminal segments of the plant anti–HIV protein GAP31, Proc. Natl. Acad. Sci. USA, 1994, 91, 12208–12212.

Lee–Huang, et al., Inhibition of the integrase of human immunodeficiency virus (HIV) type ! By anti–HIV plant proteins MAP30 and GAP31, Proc. Natl. Acad. Sci. USA, 1995, 92, 8818–8822.

\* cited by examiner

*Primary Examiner*—James Housel
*Assistant Examiner*—Shanon Foley
(74) *Attorney, Agent, or Firm*—Browdy and Neimark PLLC

(57) ABSTRACT

Truncated MAP30 or GAP31 proteins retain anti-tumor and anti-viral activity but not the cytotoxic ribosome inactivation activity. These proteins also inhibit HIV without affecting fertility of sperm.

5 Claims, 9 Drawing Sheets

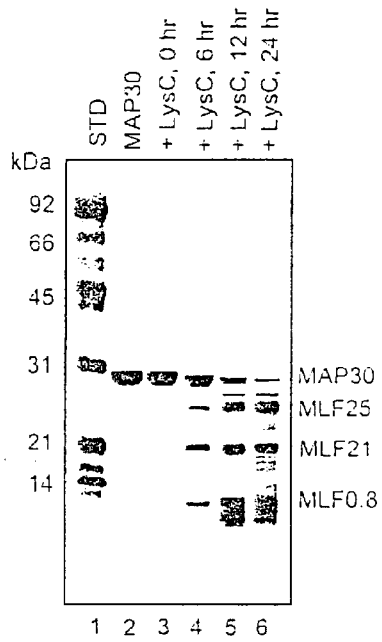
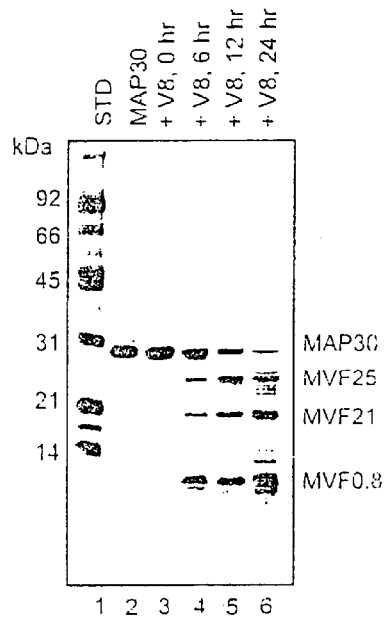
FIG. 1A
FIG. 1B
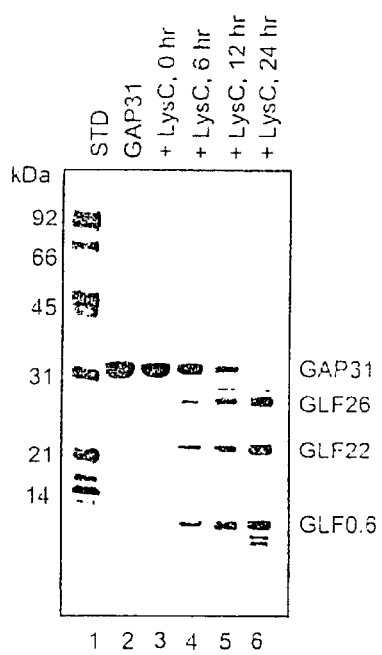
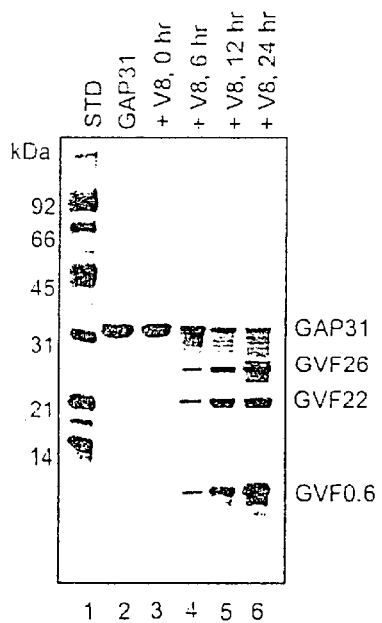
FIG. 1C
FIG. 1D

Amino Acid Sequences of GAP31 and MAP30

```
             ↓       10         20         30         40         50         60         70         80
G31  GLDT    VSFSTKGATYITYVNELNELRVKLKPEGNSHGIPLLRKKCDDPGKCFVLVALSNDNGQLAEIAIDVTSVYVVGYQV
M30   D      VNFDLSTATAKTYTKEIEDFRATLPFSHKVYDIPLLYSTISDSRR-FILLDLTSYAYETISVAIDVTNVYVVAYRT
                                                      ↑

90        100        110        120        130        140        150        160
G31  RNRSYEFKDAPDAAYEG-LEKNTI-KTRLHEGGSYPSLEGEKA-YRETTDLGIEPLRIGIKKLDENAIDNYKPTEIASSLLVV
M30  RDVSYFFKESPPE-AYNILFKGT-RKITLPYTGNYENLQTAAHKIRENIDLGLPALSSAITTLF------YYNAQSAPSALLVL

↓         ↓
             170        180        190        200        210        220        230        240
                                                                          ↓↓                    ↓
G31  IQMVSEAARFTEIENQIRNNFQQRIRPANNTISLENKWGKLSFQIRTSGAN-GMFSEAVELERANGKKYYVTAVDQ--VKPKI
M30  IQTTAEAARFKYIERHVAKYVATNEKPNLAIISLENQWSALSKQIELAQNQGGKERNPVDLIKPTGERFQVTNVDSDVVKGNI
                      ↑          ↑                     ↑                                      ↑

↓    251
G31  ALLKFVDKDPK
M30  KLLINSRASTADENFITTMTLLGESVVN
```

FIG. 5

United States Patent US 6,652,861 B1

SEQUENCE LISTING

```
<160> NUMBER OF SEQ ID NOS: 2

<210> SEQ ID NO 1
<211> LENGTH: 263
<212> TYPE: PRT
<213> ORGANISM: Momordica charantia

<400> SEQUENCE: 1

Asp Val Asn Phe Asp Leu Ser Thr Ala Thr Ala Lys Thr Tyr Thr Lys
1               5                   10                  15

Phe Ile Glu Asp Phe Arg Ala Thr Leu Pro Phe Ser His Lys Val Tyr
            20                  25                  30

Asp Ile Pro Leu Leu Tyr Ser Thr Ile Ser Asp Ser Arg Arg Phe Ile
        35                  40                  45

Leu Leu Asp Leu Thr Ser Tyr Ala Tyr Glu Thr Ile Ser Val Ala Ile
    50                  55                  60

Asp Val Thr Asn Val Tyr Val Val Ala Tyr Arg Thr Arg Asp Val Ser
65                  70                  75                  80

Tyr Phe Phe Lys Glu Ser Pro Pro Glu Ala Tyr Asn Ile Leu Phe Lys
                85                  90                  95

Gly Thr Arg Lys Ile Thr Leu Pro Tyr Thr Gly Asn Tyr Glu Asn Leu
            100                 105                 110

Gln Thr Ala Ala His Lys Ile Arg Glu Asn Ile Asp Leu Gly Leu Pro
        115                 120                 125

Ala Leu Ser Ser Ala Ile Thr Thr Leu Phe Tyr Tyr Asn Ala Gln Ser
    130                 135                 140

Ala Pro Ser Ala Leu Leu Val Leu Ile Gln Thr Thr Ala Glu Ala Ala
145                 150                 155                 160

Arg Phe Lys Tyr Ile Glu Arg His Val Ala Lys Tyr Val Ala Thr Asn
                165                 170                 175

Phe Lys Pro Asn Leu Ala Ile Ile Ser Leu Glu Asn Gln Trp Ser Ala
            180                 185                 190
```

-continued

```
Leu Ser Lys Gln Ile Phe Leu Ala Gln Asn Gln Gly Gly Lys Phe Arg
        195                 200                 205

Asn Pro Val Asp Leu Ile Lys Pro Thr Gly Glu Arg Phe Gln Val Thr
        210                 215                 220

Asn Val Asp Ser Asp Val Val Lys Gly Asn Ile Lys Leu Leu Leu Asn
225                 230                 235                 240

Ser Arg Ala Ser Thr Ala Asp Glu Asn Phe Ile Thr Thr Met Thr Leu
                245                 250                 255

Leu Gly Glu Ser Val Val Asn
                260

<210> SEQ ID NO 2
<211> LENGTH: 251
<212> TYPE: PRT
<213> ORGANISM: Gelonium multiflorum

<400> SEQUENCE: 2

Gly Leu Asp Thr Val Ser Phe Ser Thr Lys Gly Ala Thr Tyr Ile Thr
1               5                   10                  15

Tyr Val Asn Phe Leu Asn Glu Leu Arg Val Lys Leu Lys Pro Glu Gly
            20                  25                  30

Asn Ser His Gly Ile Pro Leu Leu Arg Lys Lys Cys Asp Asp Pro Gly
        35                  40                  45

Lys Cys Phe Val Leu Val Ala Leu Ser Asn Asp Asn Gly Gln Leu Ala
        50                  55                  60

Glu Ile Ala Ile Asp Val Thr Ser Val Tyr Val Val Gly Tyr Gln Val
65                  70                  75                  80

Arg Asn Arg Ser Tyr Phe Phe Lys Asp Ala Pro Asp Ala Ala Tyr Glu
                85                  90                  95

Gly Leu Phe Lys Asn Thr Ile Lys Thr Arg Leu His Phe Gly Gly Ser
            100                 105                 110

Tyr Pro Ser Leu Glu Gly Glu Lys Ala Tyr Arg Glu Thr Thr Asp Leu
            115                 120                 125

Gly Ile Glu Pro Leu Arg Ile Gly Ile Lys Lys Leu Asp Glu Asn Ala
        130                 135                 140

Ile Asp Asn Tyr Lys Pro Thr Glu Ile Ala Ser Ser Leu Leu Val Val
145                 150                 155                 160

Ile Gln Met Val Ser Glu Ala Ala Arg Phe Thr Phe Ile Glu Asn Gln
                165                 170                 175

Ile Arg Asn Asn Phe Gln Gln Arg Ile Arg Pro Ala Asn Asn Thr Ile
            180                 185                 190

Ser Leu Glu Asn Lys Trp Gly Lys Leu Ser Phe Gln Ile Arg Thr Ser
        195                 200                 205

Gly Ala Asn Gly Met Phe Ser Glu Ala Val Glu Leu Glu Arg Ala Asn
        210                 215                 220

Gly Lys Lys Tyr Tyr Val Thr Ala Val Asp Gln Val Lys Pro Lys Ile
225                 230                 235                 240

Ala Leu Leu Lys Phe Val Asp Lys Asp Pro Lys
                245                 250
```

ANTI-HIV AND ANTI-TUMOR PEPTIDES AND TRUNCATED POLYPEPTIDES OF MAP30

The present application claims priority from provisional application Ser. No. 60/150,885, filed Aug. 26, 1999.

GOVERNMENT LICENSE RIGHTS

The experiments performed in this application were supported in part by the National Institute of Allergy and Infectious Diseases, grant no. ROI AI-31343. The U.S. Government may have a paid up license in this invention and may have the right in limited circumstances to require the patent owner to license others on reasonable terms as provided by the terms of the above grant.

BACKGROUND OF THE INVENTION

1. Field of the Invention

The present invention relates to anti-HIV and anti-tumor peptides and polypeptides, as well as to peptides and polypeptides which prevent infection.

2. Description of the Related Art

Anti-HIV and anti-tumor proteins MAP30 (Momordica Anti-HIV Protein 30 kDa) and GAP31 (Gelonium Anti-HIV Protein 31 kDa) have been isolated from *Momordica charanita* and *Gelonium multiflorum*, also known as bitter melon and Himalayan fruit, respectively (Lee-Huang et al., 1990; Lee-Huang et al., 1991; U.S. Pat. Nos. 5,317,009 and 5,484,889). These medicinal plants are given orally in traditional herbal medicine. Thus the bioavailable form of these agents may be peptide fragments from proteolytic cleavage.

MAP30 and GAP31 possess multiple therapeutic targets at different stages of the HIV-1 life cycle. They act on both viral and cellular levels that may be critical to their antiviral and anti-tumor actions. The viral targets include HIV-1 integrase (Lee-Huang et al., 1995), HIV-LTR (Huang et al., 1992), v-cyclin D, v-IL6, and v-FLIP (Li et al., 1998). The cellular targets are caspases (Li et al., 1998), HER2 (Lee-Huang et al., 1999), and ribosome inactivation by N-glycosidase at A2324 of the 28S rRNA (Lee-Huang et al., 1990 and Lee-Huang et al., 1991).

While transmission of HIV can be prevented by using physical barriers during sexual intercourse, physical barriers such as condoms are not completely effective, particularly if there is a defect in the barrier which permits the virus to cross the physical barrier. Additionally, there are situations in which one party is HIV positive but there is a desire to conceive. In this type of situation a physical barrier is useless, as the physical barrier will prevent conception as well as prevent transfer of the virus form one party to the other.

Commercially available compounds for killing the human immunodeficiency virus are also spermicidal. Unfortunately, there has not beet available a method to prevent transmission of HIV while not preventing conception.

Citation of any document herein is not intended as an admission that such document is pertinent prior art, or considered material to the patent ability of any claim of the present application. Any statement as to content or a date of any document is based on the information available to applicant at the time of filing and does not constitute an admission as to the correctness of such a statement.

SUMMARY OF THE INVENTION

The present invention provides a truncated MAP30 or GAP31 protein, which is a peptide or polypeptide and which has the anti-viral and anti-tumor activities of MAP30 and GAP31 but also unexpectedly and advantageously lacks the ribosome inactivation activity that is present in native MAP30 and GAP31 protein. Moreover, this protein has been found to inhibit transmission of HIV, and it is not spermicidal. The present invention also provides for a derivative of the truncated MAP30 or GAP31 protein and a composition containing the truncated MAP30 protein, the truncated GAP31 protein, or a derivative thereof.

Further provided by the present invention are an isolated DNA molecule which encodes for the truncated MAP30 protein or truncated GAP31 protein, a transformed host cell, and a method for producing the truncated MAP30 protein or truncated GAP31 protein.

BRIEF DESCRIPTION OF DRAWINGS

FIGS. 1A–1D show the time courses of limited proteolysis of MAP30 and GAP31 with Lys-C and V8 endoproteases on SDS-PAGE. MAP30 was incubated with Lys-C (FIG. 1A), with V8 (FIG. 1B), and GAP31 was incubated with Lys-C (FIG. 1C) and with V8 (FIG. 1D) for 0, 6, 12 and 24 hr. The cleavage products were analyzed on SDS-15% polyacrylamide gels. Lane 1 is molecular weight standards; Lane 2 is MAP30 or GAP31 intact parent compounds; Lanes 3–6 are reactions for 0, 6, 12, and 24 hr respectively. Each lane contains about 8 microgram of sample. The migration positions of intact MAP30, GAP31 and the major proteolytic fragments are indicated on the right and the migration positions of molecular weight standards are shown on the left in kilodaltons (kDa).

FIG. 2A shows the elution profile of a typical 2.5 mg run of a Lys-C digest of GAP31. FIGS. 2B, 2C, and 2D show further purification of samples from peaks 1, 2, and 3, respectively, of FIG. 2A. 10 mM sodium phosphate buffer, pH 7.0, containing 0.15 M NaCl (PBS) was used as the elution buffer; the flow rate was 1 ml/min and 0.5 ml fractions were collected. Anti-HIV and anti-tumor activity was found in peaks 1 and 2, whereas peak 3 was inactive.

In FIG. 3A, anti-HIV activity was assayed by HIV core protein p24 expression in H9 cells (Lee-Huang et al., 1990 and Lee-Huang et al., 1991). The production of p24 was assayed by RIA and expressed in ng/ml and the value in control culture without the addition of the fragments was observed to be about 2186 ng/ml. Anti-tumor activity was determined by in vitro proliferation of human breast tumor MAD-MB-231 cell by [$^3$H] thymidine incorporation (Lee-Huang et al., 1999) and the average control value was about $1.88 \times 10^5$ cpm/ml (FIG. 3B). In FIG. 3C, the cytotoxic effect was measured by the MTS colorimetric assay (Lee-Huang et al., 1999), and in FIG. 3D, the ribosome-inactivation activity was determined by in vitro translation of globin message in a rabbit reticulocyte lysate system (Lee-Huang et al., 1990 and Lee-Huang et al., 1991) and the average control value was about $5.8 \times 10^4$ cpm/ml. In each assay, triplicates were carried in two independent experiments, and the results are normalized to values obtained in control assays. Standard deviations are indicated by error bars.

electrophoresis. In FIG. 4A, the inhibition on HIV-integrase was assayed by the 3'-processing reaction of HIV-1 integrase (Lee-Huang et al., 1995). This activity was assayed by specific cleavage of the dinucleotide GT from 5'-[$^{32}$P] labeled 21-mer of the HIV-U3-LTR substrate. The effect was measured by the inhibition of the formation of labeled 19-mer product by autoradiography of urea gels. Samples that inhibit the integrase reaction show only the 21-mer band, whereas samples that do not inhibit, show both the 21-mer and the 19-mer bands. In FIG. 4B, topological inactivation was measured by the conversion of supercoiled HIV-LTR DNA (S) into relaxed (R) and linear (L) forms by agarose gel electrophoresis (Huang et al., 1992). Samples that cause topological inactivation show L and R and no S forms.

FIG. 5 shows a sequence alignment of the amino acid sequences of MAP30 (SEQ ID NO:1) and GAP31 (SEQ ID NO:2) with accessible Lys-C and V8 sites. The position of lysine (K) and glutamate (E) cleavage sites are shown in bold and indicated by arrows.

DETAILED DESCRIPTION OF THE INVENTION

Figure 2A:
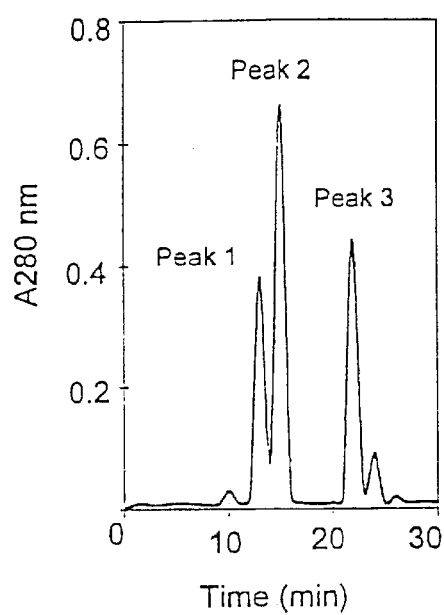
FIGS. 2A–2D show elution profiles in the purification of proteolytic fragments.

The present invention is based on the unexpected discovery by the present inventors that fragments of the anti-tumor and anti-viral MAP30 and GAP31 proteins which retain the desirable anti-tumor and anti-viral activities of the full length native MAP30 and GAP31 proteins no longer exhibit ribosome-inactivation activity. Such fragments, which are also referred to herein as truncated MAP30 or GAP31 proteins, are thus anti-tumor and anti-viral agents which advantageously lack the cytotoxicity associated with the ribosome inactivation activity of native MAP30 and GAP31. These fragments have also been found to prevent transmission of HIV, and are not spermicidal.

After much experimentation and lack of success in obtaining proteolytic fragments with many different proteases, the present inventors were finally able to achieve limited proteolysis of the unusually protease-resistant MAP30 and GAP31 proteins with the endopeptidases Lys-C and Glu-C (also known as V8). MAP30 and GAP31 were found to be resistant to proteolytic digestion under conditions of as much as 5% (W/W) proteases. In the presence of 10% (W/W) protease, however, while the central regions of the proteins were still resistant to proteolysis, the N- and C-terminus were now accessible. Peptide fragments were purified by FPLC on SUPERDEX 75 columns, characterized by gel electrophoresis, identified by amino acid sequencing and analyzed for anti-HIV, anti-tumor and other biochemical activities. The limited proteolysis with Lys-C and Glu-C yielded biologically active fragments of both MAP30 and GAP31. These fragments were found to be active against HIV-1 and tumor cells with $EC_{50}$s in the sub-nanomolar ranges, 0.2–0.4 nM. At the dose levels used in the assays, little cytotoxicity to normal cells was observed. In addition, these fragments remain fully active in HIV-integrase inhibition and HIV-LTR topological inactivation, but surprisingly not ribosome inactivation. These results obtained by the present inventors demonstrate that the antiviral and anti-tumor activity of MAP30 and GAP31 can be dissociated from ribosome inactivation activity. Thus, although portions of the N- and C-terminus are not essential for antiviral and anti-tumor activities, the C-terminus does appear to be required for ribosome inactivation.

The present invention is directed to a truncated MAP30 or GAP31 protein, which is a peptide or polypeptide, that has anti-tumor and anti-viral activity but lacks the ribosome inactivation activity of MAP30 and GAP31 proteins. From an analysis of the structural and functional organization of MAP30 and GAP31 based on the results generated by limited proteolysis with endopeptidases Lys-C and Glu-C as shown in Tables 3 and 4 of the example, it is clear that a truncated MAP30 protein, which lacks residues 233 to 263 of SEQ ID NO:1 (native full-length MAP30), and a truncated GAP31 protein, which lacks residues 227 to 251 of SEQ ID NO:2 (native full-length GAP31), have the benefit of anti-tumor and anti-viral activity without the cytotoxic ribosome inactivation activity. Preferred embodiments of the truncated MAP30 protein are those which comprise residues 13 to 187 of SEQ ID NO:1 but which lack at least residues 233 to 263. Preferred embodiments of the truncated GAP31 protein are those which comprise residues 11 to 195 of SEQ ID NO:2 but which lack at least residues 227 to 251.

It will be well-appreciated by those of skill in the art that truncated MAP30 proteins, which are themselves fragments of the truncated MAP30 protein corresponding to residues 13 to 187 of SEQ ID NO:1, and truncated GAP31 proteins, which are themselves fragments of the truncated GAP31 protein corresponding to residues 11 to 195 of SEQ ID NO:2, are also within the scope of the present invention as long as these smaller truncated MAP30 or GAP31 proteins have anti-tumor and anti-viral activities. Those of skill in the art will readily appreciate that such smaller truncated MAP30 or GAP31 proteins can be generated by the action of carboxypeptidases, by peptide synthesis, or by cloning of exonuclease-generated (5'-and/or 3'-exonucleases) nested fragments of DNA (cDNA) encoding MAP30 or GAP31.

The present invention also comprehends derivatives of the truncated MAP30 or GAP31 proteins according to the present invention. By "derivatives" is meant "chemical derivatives" and "analogs".

A "chemical derivative" contains additional chemical moieties not normally part of the MAP30 or GAP31 amino acid sequence. Covalent modifications of the amino acid sequence are included within the scope of this invention. Such modifications may be introduced into the truncated MAP30 or GAP31 protein by reacting targeted amino acid residues of the truncated protein with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxylmethyl or carboxyamidomethyl derivatives. Cysteinyl residues also are derivatized by reaction with bromotrifluoroacetone, alpha-bromo-beta-(5-imidazoyl) propionic acid, chloroacetyl phosphate, N-alkylmaleimides, 3-nitro-2-pyridyl disulfide, methyl-2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Parabromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino acid-containing residues include imidoesters, such as methyl picolinimidate, pyridoxal phosphate, pyridoxal, chloroborohydride, trinitrobenzenesulfonic acid, O-methyliosurea, 2,4-pentanedione, and transaminase-catalyzed reaction with glyoxylate.

Arginyl residues are modified by reaction with one or several conventional reagents, among them phenylglyoxal, 2,3-butanedione, and ninhydrin. Derivatization of arginine residues requires that the reaction be performed in alkaline conditions because of the high pKa of the guanidine functional group. Furthermore, these reagents may react with the groups of lysine, as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidazole and tetranitromethane are used to form O-acetyl tyrosyl species and e-nitro derivatives, respectively.

Carboxyl side groups (aspartyl or glutamyl) are selectively modified by reaction with carbodiimides (R'N-C-N-R') such as 1-cyclohexyl-3-[2-morpholinyl-(4-ethyl)] carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful for cross-linking the peptide to a water-insoluble support matrix or to other macromolecular carriers. Commonly used cross-linking agents include, e.g., 1,1-bis(diazoacetyl)-2-phenylethane, glutaraldehyde, N-hydroxysuccinimide esters, for example, ester with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizating agents such as methyl-3-[(p-azidophenyl) dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (Creighton, 1983), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable of mediating such effects are disclosed, for example, in *Remington's Pharmaceutical Sciences*, 16th ed., Mack Publishing Co., Easton, Pa. (1980).

An "analog" refers to a non-natural molecule substantially similar to the truncated MAP30 or GAP31 proteins but with one or more amino acid residues, preferably at most seven residues, more preferably at most five residues, and most preferably at most three residues, added, deleted or substituted. This "analog" has the anti-tumor and anti-viral activity of the truncated MAP30 or GAP31 protein according to the present invention.

Based on the homology observed between the amino acid sequence of MAP30 and GAP31 as shown by the sequence alignment in FIG. 5 and the amino acid comparison between MAP30, trichosanthin and ricin A chain in U.S. Pat. No. 5,484,889, a person of skill in the art would readily recognize the criticality of certain amino acids. Using the sequence identity and homology to identify conserved amino acid residues, one of skill in the art would have a range of varying homology to determine the criticality of specific residues and domains. Armed with this information, a person of skill in the art can readily identify conserved and non-conserved amino acids and make amino acids substitutions, as well as deletions or additions, accordingly. It is clear that residues that are identical in MAP30 and GAP31 in the region of residues 13 to 195 of SEQ ID NO:1 and residues 11 to 195 of SEQ ID NO:2, respectively, are to be maintained in the analogs with no substitutions or deletions. However, those of skill in the art will also appreciate that sequence homology, such as between Leu 127 of SEQ ID NO:1 and Ile 131 of SEQ ID NO:2, points to what conservative substitutions are allowed at specific residue positions. Furthermore, conservative substitutions and single residue deletions and additions in non-conserved regions can be made with a high likelihood that such change(s) would not affect the anti-tumor and anti-viral activity nor the HIV-transmission inhibition of MAP30 and GAP31.

Such substitutions preferably are made in accordance with the following list as presented in Table 1, which substitutions can be determined by routine experimentation to provide modified structural and functional properties of a synthesized or recombinant peptide polypeptide molecule, while maintaining the anti-tumor and anti-viral activities as assayed in the example herein.

TABLE 1

| Original Residue | Exemplary Substitution |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

Accordingly, based on the above example of specific substitutions, alternative substitutions can be made by routine experimentation, to provide analogs of truncated MAP30 or GAP31 protein of the present invention, e.g., by making one or more conservative substitutions.

Alternatively, another group of substitutions are those in which at least one amino acid residue in the protein molecule has been removed and a different residue inserted in its place according to the following Table 2. The types of substitutions which can be made in the truncated MAP30 or GAP31 molecule of the present invention can be based on analysis of the frequencies of amino acid changes between a homologous protein of different species or conserved amino acids between native MAP30 and GAP31. Based on such an analysis, alternative conservative substitutions are defined herein as exchanges within one of the following five groups:

TABLE 2

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val, (Cys); and
5. Large aromatic residues: Phe, Tyr, Trp.

The three amino acid residues in parentheses above have special roles in protein architecture. Gly is the only residue lacking any side chain and thus imparts flexibility to the chain. This, however, tends to promote the formation of secondary structure other than alpha-helices. Pro, because of its unusual geometry, tightly constrains the chain. It generally tends to promote beta-turn-like structures. In some cases Cys can be capable of participating in disulfide bond formation which is important in protein folding. Note that Schulz et al. would merge Groups 1 and 2 above. Note also that Tyr, because of its hydrogen bonding potential, has significant kinship with Ser, and Thr, etc.

Amino acid sequence analogs of the truncated MAP30 or GAP31 protein can be prepared by mutations in the DNA. Such analogs include, for example, deletions from, or insertions or substitutions of, residues within the amino acid sequence. Any combination of deletion, insertion, and substitution can also be made to arrive at expressing and producing the final peptide/polypeptide construct, provided that the final peptide/polypeptide construct possesses some anti-tumor and anti-viral. Obviously, the mutations that will be made in the DNA encoding the variant must not place the sequence out of reading frame and preferably will not create complementary regions that could produce secondary mRNA structure (see, e.g., EP Patent Publication No. 75,444).

At the genetic level, these variants ordinarily are prepared by site-directed mutagenesis of nucleotides in the DNA encoding the truncated MAP30 or GAP31, thereby producing DNA encoding the analog, and thereafter synthesizing the DNA and expressing the peptide/polypeptide in recombinant cell culture.

The present invention also relates to a composition which contains the truncated MAP30, the truncated GAP31 protein, or derivatives of the truncated MAP30 or GAP31 proteins. The composition further contains a pharmaceutically acceptable diluent, excipient carrier or auxiliary agent.

Suitable excipients are, in particular, fillers such as sugars, such as lactose, sucrose, mannitol, or sorbitol; cellulose preparations and/or calcium phosphates, such as tricalcium phosphate or calcium hydrogen phosphate; as well as binders such as starch paste made using, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone.

If desired, disintegrating agents may also be added, such as the above-mentioned starches as well as carboxymethyl starch, cross-linked polyvinyl pyrrolidone, agar, or alginic acid or a salt thereof, such as sodium alginate.

Auxiliaries which can be used in the compositions according to the present invention include flow-regulating agents and lubricants such as silica, talc, stearic acid or salts thereof, and/or polyethylene glycol.

Another aspect of the present invention relates to an isolated DNA molecule which encodes the truncated MAP30 or GAP31 protein of the present invention. This isolated DNA molecule can be a vector which is capable of expressing and producing the truncated MAP30 or GAP31 protein in a cultured prokaryotic or eukaryotic host cell that has been transformed with such a vector. The present invention further relates to a method for producing the truncated MAP30 or GAP31 protein by culturing a host cell transformed with-the above vector in a nutrient medium to express and produce the truncated protein followed by recovery of the expressed and produced truncated protein.

Having now generally described the invention, the same will be more readily understood through reference to the following example which is provided by way of illustration and is not intended to be limiting of the present invention.

EXAMPLE 1

To determine whether proteolytic fragments of MAP30 and GAP31 are biologically active, limited proteolysis with Lys-C and Glu-C (V8) endopeptides were carried out and a structural and activity map of MAP30 and GAP31 was constructed. The experiments performed in this study are presented below along with the materials and methods used.

Materials and Methods

Antiviral Compounds

Homogeneous MAP30 and GAP31 were prepared as described previously (Lee-Huang et al., 1990 and Lee-Huang et al., 1991). These proteins were dissolved in reaction buffers at a concentration of 10 mg/ml as stock solutions.

Proteolysis of MAP30 and GAP31

MAP30 and GAP31 were subjected to proteolysis with sequencing grade endoproteinase Lys-C and Glu-C (Promega, Madison, Wis.). Lys-C cleaves at the carboxylic side of lysine (Elliott et al., 1986). Glu-C, also known as V8 protease, cleaves specifically at the carboxylic side of glutamic acid in the presence of ammonium ion (Drapeau et al., 1972). In the absence of ammonium ion, Glu-C acts at both aspartic and glutamic acids. The reaction buffers for Lys-C and V8 were 25 mM Tris-HCl, pH 7.8, 1 mM EDTA and 50 mM ammonium bicarbonate, pH 7.8 respectively.

Characterization of Proteolytic Peptide Fragments

The proteolytic fragments were analyzed by SDS-PAGE. The N-terminal amino acid sequence was determined by Edman degradation on an automatic amino acid sequencer. The C-terminal amino acid was determined enzymatically by carboxypeptidases B and Y (Worthington, N.J.).

Electrophoresis, Electroblotting and Amino Acid Sequencing

SDS-PAGE was carried out on 15% polyacrylamide separating gels containing 0.1% SDS (w/v) in 0.375 M Tris, pH 8.8 with 4% stacking gels containing 0.1% SDS (w/v) in 0.125 M Tris, pH 6.8 (Laemmli, 1970). Electrophoresis was performed in Tris-glycine buffer (25 mM Tris, pH 8.3, 192 mM glycine) containing 0.1% SDS, at 100 V for 2.5 hr. For visual analysis, the gels were transferred to Immobilon-P membranes by electroblotting (Wong et al., 1989). Electroblotting was carried out at a constant voltage of 50 V for 1 hr. The blot was stained and individual bands were cut out, eluted from the membrane and subjected to N-terminal amino acid sequencing using the Applied Biosystem Automatic Sequencer Model 494, according to manufacturer's procedures.

Purification of Proteolytic Peptide Fragments

Peptide fragments were purified by FPLC on a SUPERDEX 75 10/30 column equilibrated with 10 mM phosphate, pH 7.0, containing 0.15 M NaCl (PBS). The column was eluted at a flow rate of 1 ml/min and fractions of 0.5 ml were collected. Fractions were pooled, concentrated, and then assayed for anti-HIV, anti-tumor and other bioactivities. The pool fractions in each peak were subjected to rechromatography on SUPERDEX 75 10/30 column so as to yield homogeneous fragments.

Bioassays

Anti-HIV activity was determined by inhibition on the expression of viral core protein p24 expression by RIA (Lee-Huang et al., 1990; Lee-Huang et al., 1991 and Lee-Huang et al., 1999). Anti-tumor activity was determined by the effects of the peptide fragments on the growth of human breast tumor cell line MDA-MB-231 by [$^3$H] thymidine incorporated (Lee-Huang et al., 1999 and Rybak et al., 1994). HIV-integrase inhibition was assayed by the three specific reactions catalyzed by the integrase, namely, 3' processing (specific cleavage of the dinucleotide GT from the viral substrate HIV-LTR U3), strand transfer (integration) and disintegration (Lee-Huang et al., 1995). Topological inactivation was measured by the conversion of supercoiled HIV-LTR DNA to relaxed and linear forms (Huang et al., 1992). Ribosome inactivation was determined by the translation of globin message in a rabbit reticulocyte lysate system (Lee-Huang et al., 1990 and Lee-Huang et al., 1991).

Cytotoxicity and Cell Viability

Cytotoxicity/cell viability was determined by the MTS assay (Cory et al., 1991).

Results

Mapping of Sensitive Proteolytic Cleavage Sites

To define the structural and activity domains of anti-HIV proteins MAP30 and GAP31, peptide fragmentation by limited proteolysis with Lys-C and V8 was performed, the cleavage products were analyzed by SDS-PAGE, and the fragments were identified by N- and C-terminal amino acid sequencing.

MAP30 and GAP31 are resistant to proteases, and no proteolysis was detected up to 24 hr of treatment even at as much as 5% (W/W) of enzyme. However, incubation with 10% (W/W) of proteases resulted in limited fragmentation. FIGS. 1A–1D show time course SDS-PAGE patterns of Lys-C and V8 digestions of MAP30 and GAP31. Three major fragments were produced in each case. These fragments are designated MLF25, MLF21, MLF0.8 (MAP30 Lys-C Fragments of 25, 21, and 0.8 kDa, FIG. 1A), MVF25, MVF21, MVF0.8 (MAP30 V8 Fragments of 25, 21, and 0.8 kDa, FIG. 1B), GLF26, GLF22, GLF0.6 (GAP31 Lys-C Fragments of 26, 22 and 0.6 kDa, FIG. 1C), and GVF26, GVF22, GVF0.6 (GAP31 V8 Fragments of 26, 22 and 0.6 kDa, FIG. 1D). The smaller peptides are C-terminal fragments produced during proteolysis and they are sensitive to further digestion to short peptides. The central core fragments, MLF25, MVF21, GLF 26 and GVF 22 are resistant to proteolysis and remained intact even after 24 hr of proteolysis.

The results of N- and C-terminal amino acid sequence analyses are summarized in Table 3. Both the terminal regions of MAP30 and GAP31 are accessible to proteolysis, and cleavages were detected at many of the predicted sites. However, the central portions of the proteins are resistant. Proteolytic fragments spanning these regions remained intact throughout the entire time course during proteolysis.

TABLE 3

Amino Acid Sequence of MAP30 and GAP31 Proteolytic Fragments

| Fractions* | SDS-PAGE Position | N-Terminus Sequence | C-Terminus Sequence | Fragment Location (Residues Positions) | Anti-HIV Activity |
|---|---|---|---|---|---|
| MLF25 | 24–25 kDa | TYTKFIEDFRAT... | KVV | 13–232 of SEQ ID NO:1 | + |
| MLF21 | 20–21 kDa | TYTKFIEDFRAT... | KSL | 13–195 of SEQ ID NO:1 | + |
| MLF0.8 | ~0.76 kDa | (Q)IFLA(Q)N(Q)GGKF... | NVV | 196–263 of SEQ ID NO:1 | − |
| MVF25 | 24–25 kDa | DVNFDLSTATAK... | EGT | 1–219 of SEQ ID NO:1 | + |
| MVF21 | 20–21 kDa | DVNFDLSTSTAK... | ELS | 1–187 of SEQ ID NO:1 | + |
| MVF0.8 | ~0.84 kDa | N(Q)WSALSK(Q)IFP... | NVV | 188–263 of SEQ ID NO:1 | − |
| GLF26 | 25–26 kDa | GATYITYV(N)FLNE... | KGN | 11–226 of SEQ ID NO:2 | + |

TABLE 3-continued

Amino Acid Sequence of MAP30 and GAP31 Proteolytic Fragments

| Fractions* | SDS-PAGE Position | N-Terminus Sequence | C-Terminus Sequence | Fragment Location (Residues Positions) | Anti-HIV Activity |
|---|---|---|---|---|---|
| GLF22 | 21–22 kDa | GATYITYV(N)FLNE . . . | KGW | 11–200 of SEQ ID NO:2 | + |
| GLF0.6 | ~0.56 kDa | LSF(Q)IRTSGA(N)GM . . . | KPD | 201–251 of SEQ ID NO:2 | – |
| GVF26 | 25–26 kDa | GLDTVSFSTKGA . . . | EVA | 1–219 of SEQ ID NO:2 | + |
| GFV22 | 21–22 kDa | GLDTVSFSTKGA . . . | ELS | 1–195 of SEQ ID NO:2 | + |
| GVF0.6 | ~0.6 kDa | (N)KWGKLSF(Q)IRT . . . | KPD | 196–251 of SEQ ID NO:2 | – |

(N) and (Q) were not identified during sequencing by the Edman degradation.
*MLF = MAP30 Lys-C Fragment MVF = MAP30 V8 Fragment. GLF = GAP31 Lys-C Fragment GVF = GAP31 V8 Fragment and the numbers indicated approximate kDa of the fragments. Anti-HIV activity was determined as described in the Materials and Methods.

Purification of Proteolytic Fragments

Figure 2B:
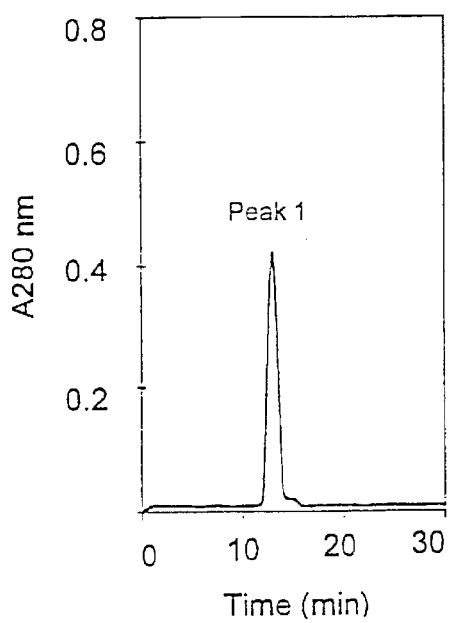
Figure 2C:
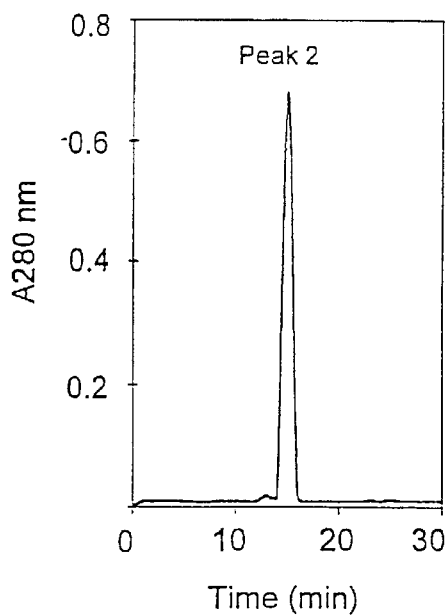
Figure 2D:
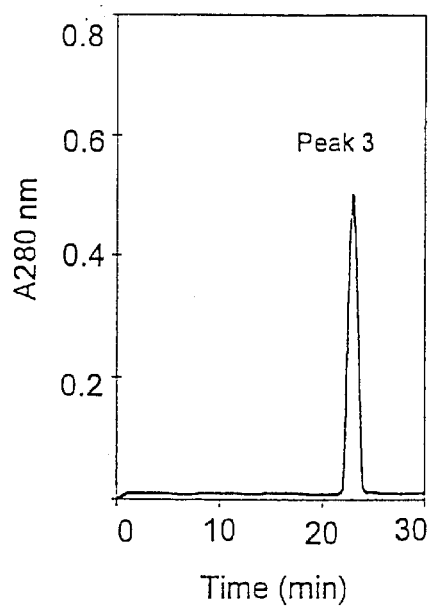

The proteolytic fragments produced by limited digestion of MAP30 or GAP31 with Lys-C or V8 were resolved by FPLC on a SUPERDEX 75 HR 10/30 column. Although the proteolytic sites are unique in each case, the size of the fragments are similar, indicating that the folding and the interdomain regions of these proteins are similar. A typical elution profile of the proteolytic digest is shown in FIG. 2A, which represents the elution profile of a Lys-C digest of GAP31. Three major peaks and several minor peaks were detected. Peaks 1, 2 and 3 correspond to fragments 26, 22 and 0.6 kDa respectively. The eluted fractions of each peak were pooled and assayed for anti-HIV, anti-tumor and other bioactivities. Most of the anti-HIV and anti-tumor activity was found in peaks 1 and 2 while no activity was found in peak 3 (FIGS. 2B–2D), and the minor peaks.

Samples from peaks 1, 2 and 3 were further purified to homogeneous fragments, were subjected to N- and C-terminal amino acid sequencing to confirm their identities and to bioassays to determine their $EC_{50}$ in antiviral and anti-tumor activities.

Proteolytic Fragments of MAP30 and GAP31 are Active Against HIV and Tumor Cells

Figure 3A:
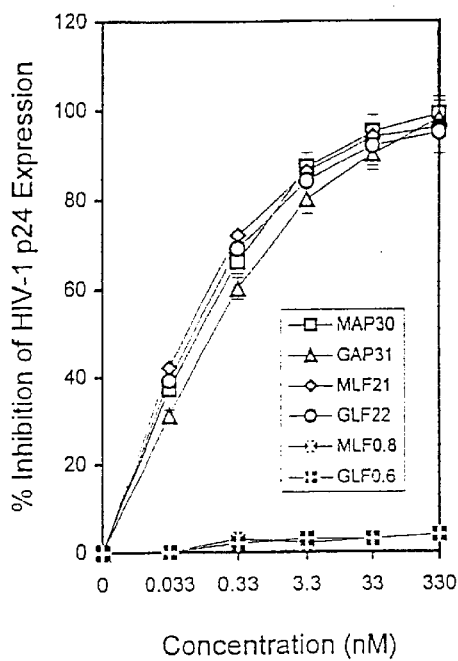
FIGS. 3A–3D show that proteolytic fragments of MAP30 and GAP31 have anti-HIV and anti-tumor activities but are not cytotoxic do not have ribosome inactivation activity.
Figure 3B:
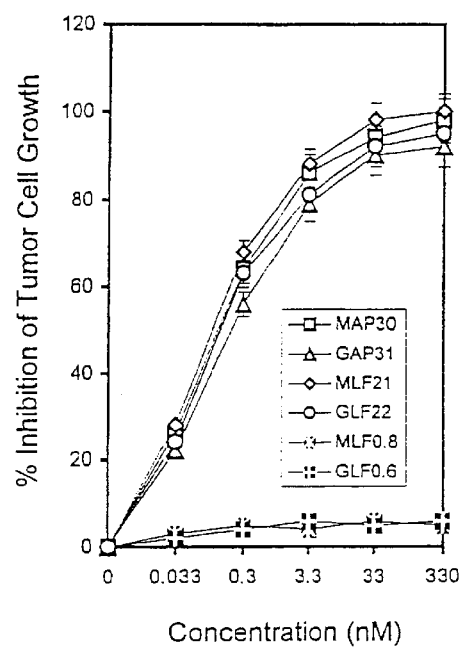

To analyze the structural and activity relationship of the anti-HIV proteins, each of the homogeneous proteolytic fragments was assayed for anti-HIV and anti-tumor activities. A dose range from 0.033 to 330 nM was studied in order to compare the potencies of the fragments with those of their intact parent compounds. Anti-HIV activity was measured by viral core protein p24 expression in HIV-1 infected H9 T lymphocytes by RIA (Lee-Huang et al., 1990 and Lee-Huang et al., 1991). Anti-tumor activity was measured by proliferation of human breast tumor MDA231 cells (Lee-Huang et al., 1999 and Rybak et al., 1994). Fragments MLF25, MLF21, MVF25, MVF21, as well GLF26, GLF22, GVF26, GVF22, exhibit comparable effects on the inhibition of viral production and tumor proliferation as intact MAP30 and GAP31, with $EC_{50}$ (effective concentration at 50% inhibition) in the range of 0.2–0.4 nM. No significant difference in the anti-HIV and anti-tumor activities was detected between these core fragments. The C-terminal fragments MLF0.8, MVF0.8, GLF0.6, and GVF0.6 on the other hand, exhibited neither anti-HIV nor anti-tumor activity. Typical dose response curves for the anti-HIV and anti-tumor activities of representative fragments are shown in FIGS. 3A and 3B respectively. These results indicate that core fragments MLF21, MVF21, GLF22, and GVF22 are sufficient for full anti-HIV and anti-tumor activities, whereas the N-terminal 10 amino acids of both MAP30 and GAP31 as well as the C-terminal 76 amino acids of MAP30, and 56 amino acids of GAP31 are not required.

The Proteolytic Fragments of MAP30 and GAP31 are not Cytotoxic

To ensure that the anti-HIV and anti-tumor action of the core fragments of MAP30 and GAP31 is not due to non-specific inhibition of cell proliferation, their effect on target cell proliferation by the MTS assay was examined (Cory et al., 1991).

Figure 3C:
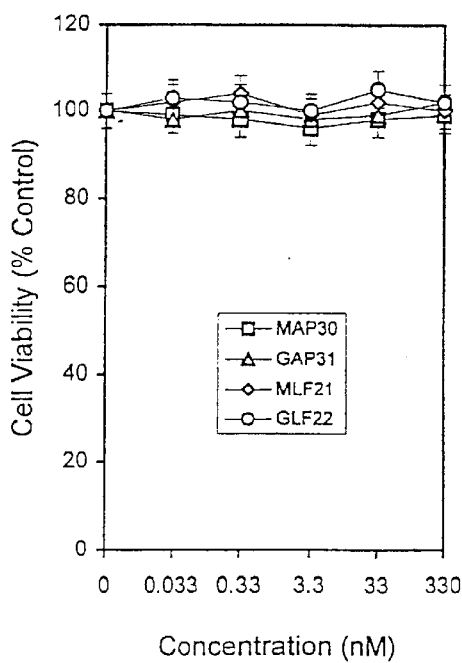

As seen in FIG. 3C, no cytotoxic effect was detected for these core fragments over the entire concentration range of the anti-HIV and anti-tumor assays.

Figure 3D:
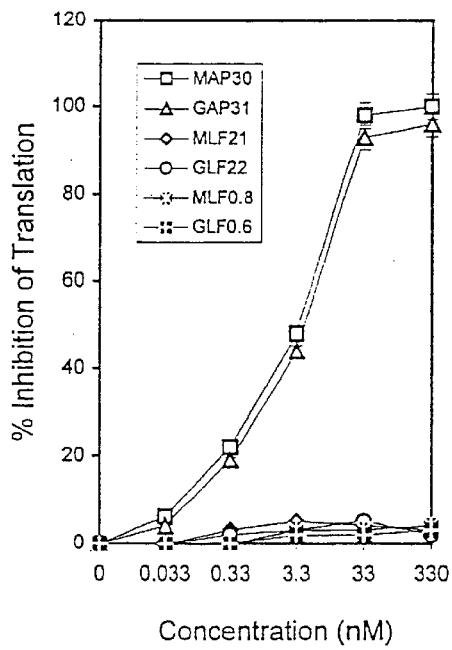
Figure 4A:
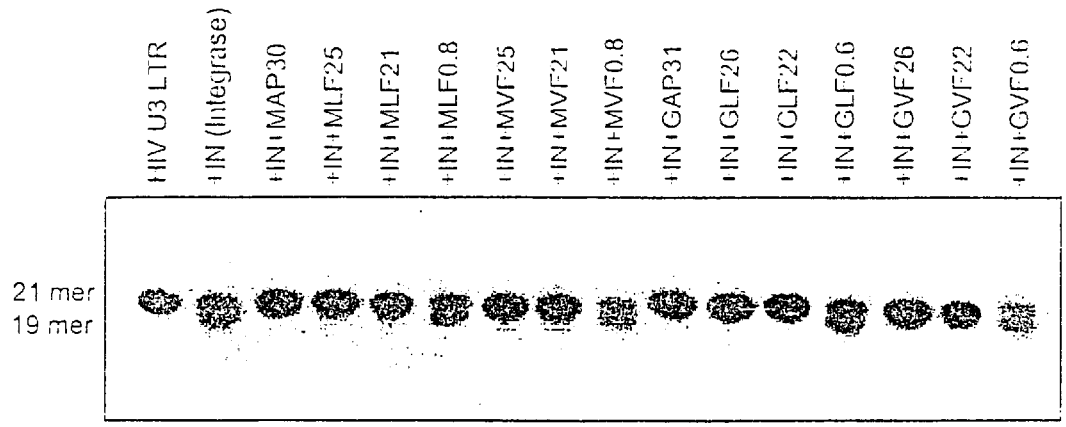
FIGS. 4A and 4B show that anti-HIV and anti-tumor proteolytic fragments of MAP30 and GAP31 are active in HIV-integrase inhibition and HIV-LTR topological inactivation on urea gel (FIG. 4A) and agarose gel (FIG. 4B)
Figure 4B:
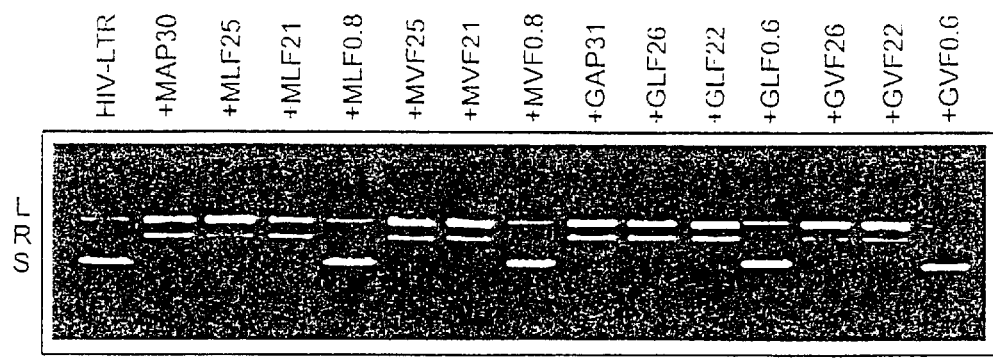

Anti-HIV and Anti-tumor Activities can be Dissociated From Ribosome Inactivation The proteolytic fragments were tested for other biochemical activities found in MAP30 and GAP31 including HIV-integrase inhibition, DNA topological inactivation, and ribosome inactivation. The results are shown in FIGS. 4A, 4B and FIG. 3D and are summarized in Table 4.

TABLE 4

Bioactivities of MAP30 and GAP31 Proteolytic Fragments

| Fragment* | Location | Anti-HIV[1] | Anti-tumor[2] | Integrase Inhibition[3] | Topo-Inact[4] | RNP-Inact[5] |
|---|---|---|---|---|---|---|
| MLF25 | T13---232 | + | + | + | + | – |
| MLF21 | T13---K195 | + | + | + | + | – |
| MLF0.8 | Q196---N263 | – | – | – | – | – |
| MVF25 | D1---E219 | + | + | + | + | – |
| MVF21 | D1---187 | + | + | + | + | – |
| MVF0.8 | N188---N263 | – | – | – | – | – |
| GLF26 | G11---K226 | + | + | + | + | – |
| GLF22 | G11---K200 | + | + | + | + | – |
| GLF0.6 | L201---K251 | – | – | – | – | – |
| GVF26 | G1---E219 | + | + | + | + | – |
| GVF22 | G1---E195 | + | + | + | + | – |
| GVF0.6 | N196---K251 | – | – | – | – | – |

*MLF = MAP30 Lys-C Fragment, MVF = MAP30 V8 Fragment, GLF = GAP31 Lys-C Fragment, GVF = GAP31 V8 Fragment and the numbers indicate approximate kDa of the fragments.
[1]Anti-HIV activity was determined by HIV-1 core protein p24 production in HIV-infected H9 cells.
[2]Anti-tumor activity was measured by the proliferaton of human breast tumor cell MDA231.
[3]Integrase inhibition activity was assay by 3'-processing, strand transfer and disintegration.
[4]Topological inactivation activity was determined by the conversion of supercoiled HIV-LTR DNA into relaxed and linear forms.
[5]Ribosome inactivaton was determined by the translation of globin message in a rabbit reticulocyte lysate system.

The anti-HIV and anti-tumor fragments, MLF25, MLF21, MVF25, MVF21, GLF26, GLF22, GVF26, GVF22 are active in HIV-integrase inhibition as assayed by the 3'-processing (FIG. 4A), strand transfer and disintegration (data not shown) as well as in DNA topological inactivation as assayed by the conversion of supercoiled HIV-LTR into relaxed and linear forms (FIG. 4B). However, none of these fragments are active in ribosome inactivation as assayed by the incorporation of [$^3$H]-labelled leucine in a rabbit reticulocyte lysate translation system using globin message (FIG. 3D). These results indicate that the antiviral and anti-tumor activities of MAP30 and GAP31 can clearly be separated from their ribosome inactivation activity. Moreover, the C-terminal regions of these proteins are required for N-glycosidase activity, but not for antiviral and anti-tumor activities.

Analysis of Structural and Activity Relationship

Figure 6:
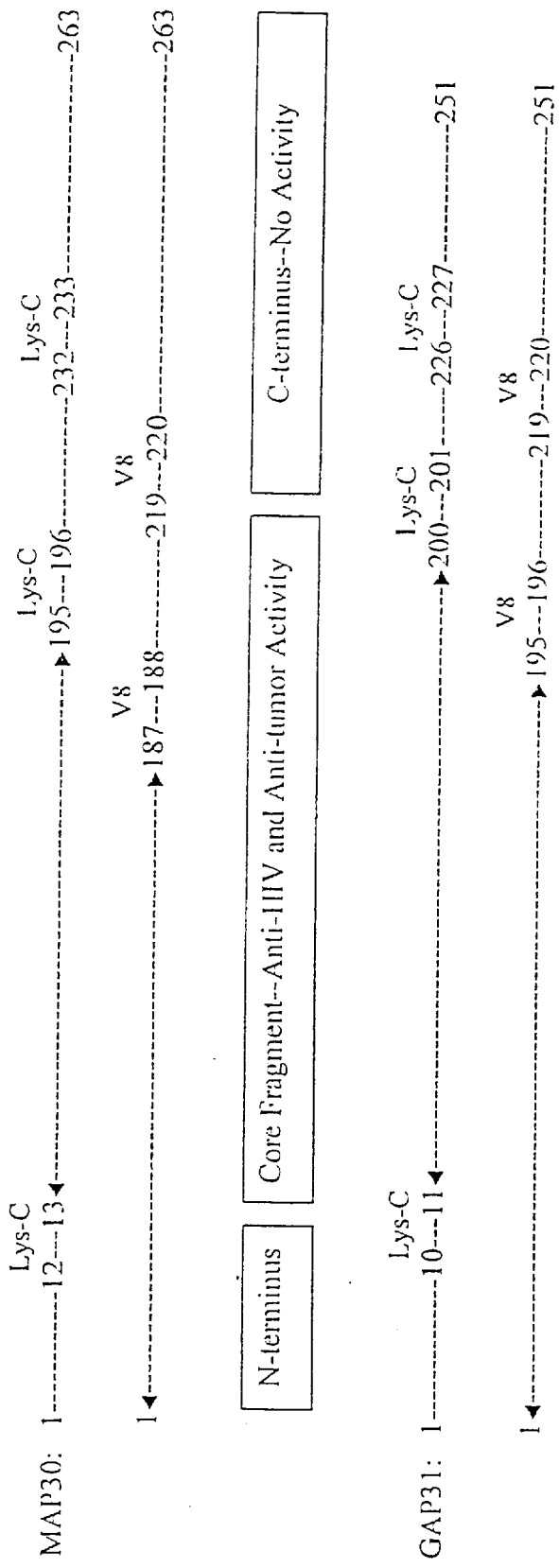
FIG. 6 shows a schematic representation of the structure and activity map of MAP30 and GAP31 with the proteolytic cleavage sites and the location of the fragments in the anti-HIV proteins MAP30 or GAP31 shown.
Figure 7:
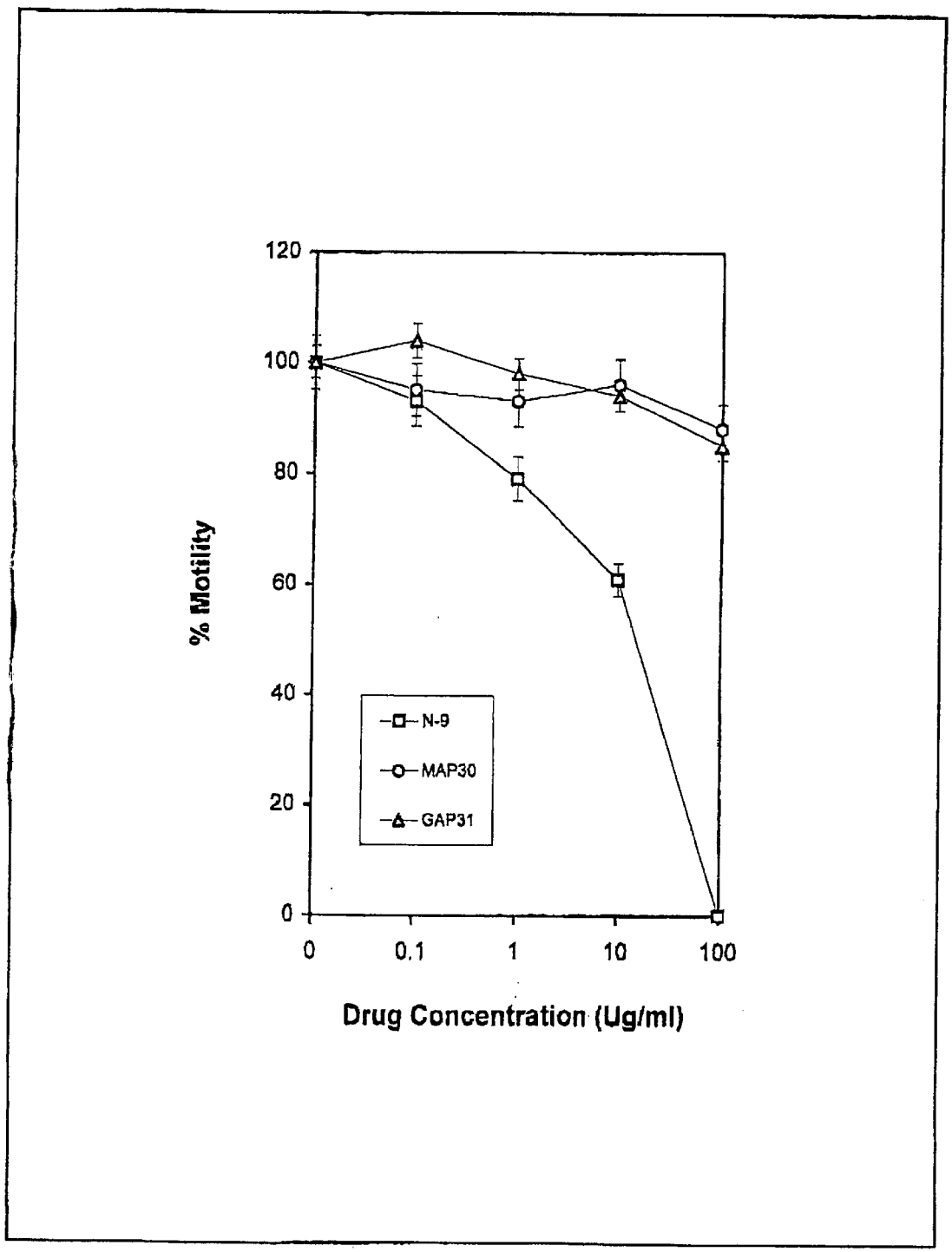
FIG. 7 shows the effect of N-9, MAP30 and GAP31 on the motility of human spermatozoa. The plot represents average values of data triplicate measurements of duplicate experiments form ten individual human sperm samples at each of the drug concentrations. All data are expressed as the mean+standard error of the mean (SEM). The inhibition of sperm motility by N-9 is dose-dependent. Complete inhibition was achieved at 100 micrograms/ml, whereas MAP30 and GAP31 demonstrated little inhibition over the entire concentrations tested.
Figure 8:
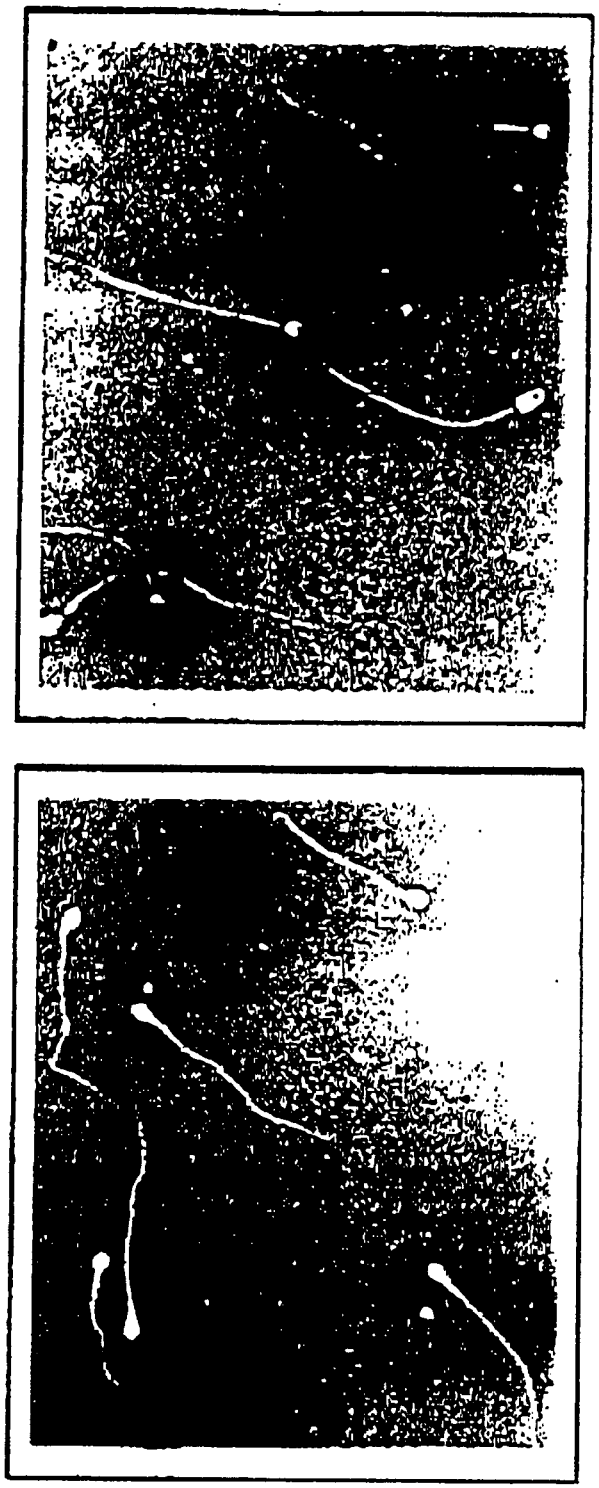
FIG. 8 shows the effect of N-9 and GAP31 on the vitality of human spermatozoa. The sperm samples were stained with vital stain. Pictures shown are at about 800× magnification. N-9, a potent spermicide, exhibits strong anti-sperm effect. Upon treatment with N-9, all sperm wimples were dead and permeable to the pink eosin Y dye in the stain. GAP31 was not toxic to the spermatozoa, and had little effect on the vitality of the sperm. Samples treated with GAP31 remained vital and impermeable to eth dye in the stain. Identical results were obtained with MAP30 and with untreated control samples.
Figure 9:
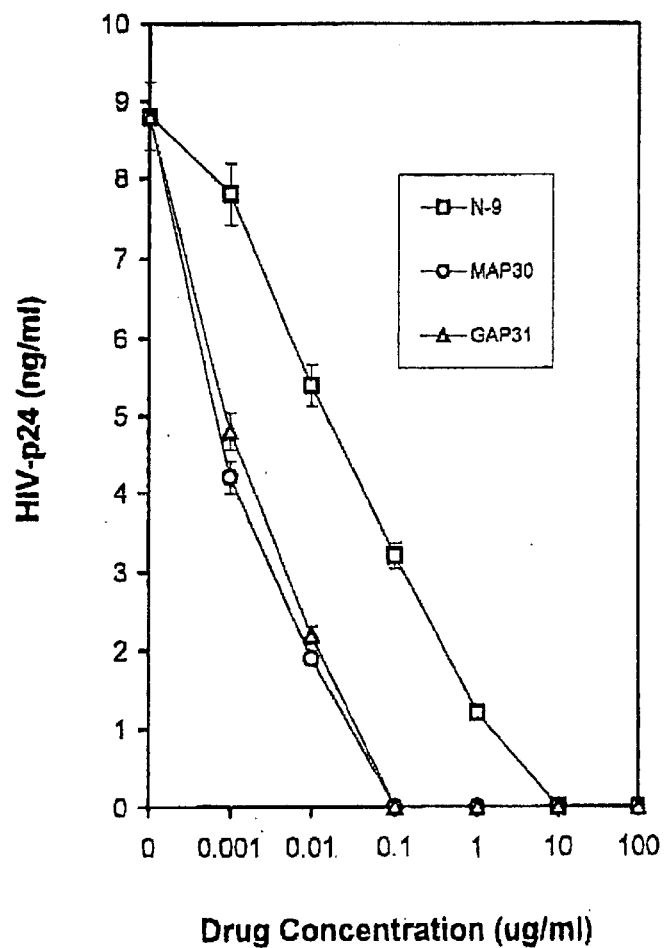
FIG. 9 shows the effect of N-9, MAP30 and GAP31 on HIV-1 as assayed by p24 ELISA of HIV-infected MT4 culture supernatant. The plot represents average values of duplicate measurements form three independent experiments. All data are expressed as the mean+standard error of the mean (SEM). Complete inhibition of p24 expression by MAP30 or CAP31 is observed at 0.1 microgram/ml, whereas for N-9 it is about 100-fold higher, at 10 micrograms/ml.

MAP30 and GAP31 contain amino acid residues that are conserved between these proteins. FIG. 5 shows an alignment of the amino acid sequence of MAP30 and GAP31. The resistance of these compounds to proteolytic attack by Lys-C and V8 is apparently not due to a lack of cleavage sites because there are 15 lysine and 12 glutamic acid residues scattered throughout the MAP30 molecule, and 22 lysine and 16 glutamic acid residues in the GAP31 molecule. Resistance of proteolysis to Lys-C and V8 likely indicates that MAP30 and GAP31 are rigidly packed, making them relatively inaccessible to proteolytic cleavage, especially in the core region. As seen in FIG. 6, the accessible proteolytic sites are located in both the N- and C-terminus, whereas the core domains are more resistant. Proteolytic fragments spanning this region remained intact upon overnight proteolysis and this region is fully active in anti-HIV, anti-tumor, integrase inhibition, HIV-LTR topological inactivation, but not active in ribosome inactivation.

EXAMPLE 2

Materials and Methods

Semen Samples and Counting

Ten semen samples were randomly obtained form ten donors at the Andrology laboratory of the Department of Obstetrics and Gynecology at NYU Medical Center. All specimens were normal semen samples according to WHO guidelines. Each sample consisted of greater than or equal to 20 million motile sperm per milliliter. Sperm count and motility were determined by placing the sperm on a hackler chamber and assessing the samples under a 40× power microscopic field.

Each semen sample was washed two consecutive times in Ham's F-10 media. The washed sperm was spun to a pellet and then re-suspended in media to a concentration of 40 million spermatocytes per milliliter with at least 50% motility. Five microliters of sperm were then suspended in 100 microliters each of PBS, serial 10-fold dilutions of MAP30, or GAP31 or N-9 from 100 to 0.1 microg/ml. N-9 was used as a positive control. Motility and forward progression were assessed at each log concentration of the three compounds. The exposure time ranged form five minute to two hours.

Vital Staining

The vitality staining was carried out by adding two drops of eosin Y to one drop of sperm sample and mixing for ten seconds. Two drops of nigrosine were then added to this mixture, and the solutions as mixed for 30 seconds. Slides were made from one drop of each solution mixed with MAP30, or GAP31, or N-9.

Antiviral Compounds

Homogeneous MAP30 (Momordica Anti-HIV Protein, MW 30 kD) and GAP31 (Gelonium Anti-HIV Protein, MW 31 kD) were prepared as described earlier (Lee-Huang et al (1990); Lee-Huang et al (1991)). These samples were dissolved in sterile PBS at a concentration of 1 mg/ml as stock solutions and kept at 4° C. until used. Nonoxynol-9 was purchased from Sigma (St. Louis, Mo.) and prepared as 1 mg/ml stock solution.

Anti-HIV Assay

Anti-HIV activity was assayed by inhibition on viral core protein, p24 expression in HIV-infected MT-4 T lymphocytes by RIA as described previously (World Health Organization (1992); Bourinbaiar et al (1995)). Briefly, the cells were plated in duplicated in 96-well microtiter plates at 1×10$^5$ cells/ml in the presence of serial 10-fold dilution of MAP30, or GAP31 or NP-9 at concentrations from 10 µg to 10 µg/ml. The cells were then infected with HIV-1(IIIB) at 100 infectious units per cell. The culture supernatants were collected on day 3 and were used for p24 assay using ELISA kit from Coulter (Hialeah, Fla.). Duplicates of original viral inoculum in the same volume of the medium without the target cells and incubated for 3 days were used as blanks. The blank values were subtracted from wells in which virus was propagated in host MT4 cells with or without drugs.

Anti-HSV Assays

Anti-HSV activity was assayed with HSV-2 by ELISA (Meridian Diagnostics, Inc., Cincinnati, Ohio) as reported previously (Bourinbaiar et al (1996)). Human embryonic lung fibroblast cell line WI-38, (CCL-75, from ATCC, Rockville, Md.) was used as target cells. HSV-2 (VR-734, strain G) derived from a human with the genital infection was obtained from ATCC, Rockville, Md.

Results

MAP30 and GAP31 are not Toxic to Human Spermatozoa

Sperm Motility by Counting

The effect of N-9, MAP30 and GAP31 on the motility of 10 different semen samples collected from 10 individual donors over concentration ranges of three logs from 0.1 to 100 µg/ml are summarized in FIG. 1. All values are expressed as percentages of relative motility, using results from samples in PBS as 100% motility. All data are expressed as mean ± standard error of the mean (SEM) of three measurements of duplicate samples at each concentration. At 100 µg/ml, N-9 totally inhibited the motility of the sperm cells from all of the ten samples whereas MAP30 and GAP31 showed only marginal effect. At 10 µg/ml, the EC100 of N-9's antiviral activity, N-9 caused 43±5% inhibition in motility, while MAP30 and GAP31 caused 4 to 6±4% inhibition. At lower concentrations from 1 to 0.01 µg/ml, the effective antiviral ranges for MAP30 and GAP31, practically no inhibition (0 to 3%) on sperm motility was observed. N-9, however, exhibited dose-dependent inhibition of sperm motility. These results illustrate clearly that in contrast to N-9, antiviral agents MAP30 and GAP31 are not toxic to human spermatozoa. The trend and tenor of the data are generally in good correlation. The variations are within the limits of experimental accuracy. It is clear that there is a dose-response spermicidal effect of N-9 and a lack of effect of MAP30 and GAP31. The effective concentrations for 50% (EC50) and 100% (EC100) inhibition for the spermicidal activity of N-9 are 20 µg/ml and 100 µg/ml, respectively. These values are consistent with previously reported results (Lee (1996)). However, MAP30 and GAP31 showed little spermicidal activity over the entire concentration ranges tested.

Sperm Vitality by Staining

To confirm MAP30 and GAP31 are not toxic to human spermatozoa, in addition to motility studies by sperm counting, we carried out studies by vitality staining. FIG. 2 represents typical staining results. As seen in this figure, treatment of human sperm samples with N-9 resulted in potent spermicidal effect and the dead sperms' membranes are permeable to the pink stain. Whereas GAP31 and MAP30 treated spermatozoa remained vital and impermeable to the pink dye of the stain.

Antiviral Activity

The anti-HIV activity of MAP30 and GAP31 was compared with that of N-9 by measuring their effect on the expression of viral core protein p24 expression in HIV-1 infected MT4 lymphocytes. The results are summarized in FIG. 3. Over a 10,000-fold concentration range, from 0.001–10 μg/ml (0.03–334 nM), MAP30, GAP31 and N-9 all exhibit dose-dependent inhibition on p24 production. GAP31 and MAP30 exerted similar anti-HIV effect with EC50s and EC100s of 0.001 and 0.1 μg/ml (0.3 and 3.3 nM), respectively. In comparison to the commonly used spermicidal agent, N-9, EC50 and EC100 of 0.1 and 10 μg/ml (162 nM and 16.2 μM, respectively), MAP30 and GAP31 are about 100-fold more potent than N-9 in terms of weight per volume. In terms of molar concentration, GAP31 and MAP30 are about 540-fold more potent than N-9 at EC50.

Comparison of Antiviral and Spermicidal Activities of MAP30, GAP31 and N-9

The antiviral activity of MAP30, GAP31 and N-9 and the comparison of their spermicidal activity are summarized in Table 1. The EC50 and EC100 of HIV-1 and HSV infection for N-9 were higher than that of MAP30 or GAP31. Complete inhibition of HIV-1 and HSV-2 by N-9 was observed at dosages of 10 μg/ml and 50 μg/ml, respectively. At these concentrations, N-9 caused about 50 to 80% inhibition on sperm motility. As for MAP30 and GAP31, EC100s of 0.08 and 0.1 μg/ml for HIV-1 and 0.01 and 0.1 μg/ml for HSV-2 were obtained, respectively. These concentrations are two to three orders of magnitudes lower than the EC100 for N-9, and at these concentrations no significant effect on sperm motility can be detected. It is important to note that these results indicate that not only are MAP30 and GAP31 more potent than N-9 in antiviral action, but they are also non-spermicidal.

DISCUSSION

In this study, the structure-activity relationship of anti-HIV proteins MAP30 and GAP31 by limited proteolysis was investigated. Proteolytic fragments of MAP30 and GAP31 generated by Lys-C and V8 were characterized and their biological activities in anti-HIV, anti-tumor, HIV-integrase inhibition, HIV-LTR topological inactivation and ribosome inactivation were mapped. It was found that limited proteolysis of these anti-HIV proteins with Lys-C and V8 yielded peptide fragments that are active against HIV-1 and tumor cells. These fragments are also active in HIV-integrase inhibition and HIV-LTR topological inactivation but not in ribosome inactivation. This is the first evidence showing that anti-HIV and anti-tumor peptides can be generated by endopeptidases of the gastrointestinal tract. A functional domain for anti-HIV and anti-tumor activities was identified in these agents which is devoid of ribosome inactivation activity.

The separation of the antiviral and anti-tumor activates of MAP30 and GAP31 from their ribosome inactivation activity is of great significance. It demonstrates that the antiviral and anti-tumor effects do not depend on ribosomal inactivation. This will enable rational design and targeted development of peptide fragments with specific targets present in viral infected and/or tumor cells while remaining free of cytotoxicity to normal cells.

In studying the structure of MAP30 (Wang et al., 1999) GAP31 (Lee-Huang et al., 1994), sequence and structural homology were detected between these proteins and the superfamily of single chain ribosome inactivating proteins (SCRIPs) also known as type I RIPs (ribosome inactivating proteins) including momordin, trichosanthin, and pokeweed antiviral protein (PAP) (Mlsna et al., 1993; Husain et al., 1994; Zhou et al., 1994 and Monzingo et al., 1993). The three-dimensional organization of the putative active center for ribosome inactivation is highly conserved between SCRIPs and the catalytic A chain of ricin, a type II RIP (Mlsna et al., 1993; Husain et al., 1994; Zhou et al., 1994 and Monzingo et al., 1993). Thus many SCRIPs including MAP30 and GAP31 are often misconstrued as toxic analogous of the toxin ricin. However, ricin and SCRIPs such as MAP30 and GAP31 differ significantly in their biological function and substrate specificity. MAP30 and GAP31 are potent antiviral and anti-tumor agents; they are specific against viral-infected and tumor cells, yet not toxic to normal and uninfected cells (Lee-Huang et al., 1990; Lee-Huang et al., 1991; Lee-Huang et al., 1995; Huang et al., 1992; Li et al., 1998; Li et al., 1998; Lee-Huang et al., 1999 and Elliott et al., 1986). Ricin A chain, on the other hand, has no antiviral and anti-tumor activity, and is extremely toxic to normal cells (Chaddock et al., 1996 and Lee-Huang et al., 1992). The N-glycosidase activity of RIPs that specifically depurinates A4324 of the 28S rRNA, leading to ribosomal inactivation and inhibition of protein biosynthesis, is responsible for potent toxicity of ricin A chain and other RIPs (Day et al., 1996 and Montfort et al., 1987). The results in this study indicate that the structural/functional requirements of antiviral and anti-tumor activities can be dissociated from ribosome inactivation, and may explain why MAP30 and GAP31 do not show the toxicity observed with ricin A chain and other SCRIPs.

MAP30 and GAP31 act on both viral DNA and RNA. Their DNA and RNA binding sites are distinct from those involved in ribosome inactivation (Lee-Huang et al., 1994). The RNA binding site of PAP is also different from its ribosome inactivation domain (Tumer et al., 1997). These results demonstrate clearly that an intact ribosome inactivation active site is not a prerequisite to antiviral activity and vice versa. Thus, ricin A chain does not have antiviral activity.

Further evidence that ribosome inactivation is not relevant to the antiviral and anti-tumor activities comes from comparing their $E_{50}$s. The $EC_{50}$s for RIP activity of MAP30 and GAP31 are at least ten times higher than that for their anti-HIV activity (Lee-Huang et al., 1990 and Lee-Huang et al., 1991). MAP30 and GAP31 inhibit HIV-1 infection and replication at concentrations that showed little effect on ribosome-inactivation (Lee-Huang et al., 1990 and Lee-Huang et al., 1991). PAP inhibits HIV-1 production of p24 at concentrations that do not adversely affect protein synthesis (Zarling et al., 1990). Animal studies also indicate differences in dose response of PAP for protein synthesis inhibition as compared with viral production (Aron et al., 1980).

It was also discovered that antiviral agents MAP30 and GAP31 do not affect the motility and vitality of human sperm cells.

There is a compelling reason to develop vaginal microbicides with antiviral specificity for preventing sexual transmission of HIV and other sexually transmitted diseases. Most vaginal virucides, however, as spermicides with anti-fertility effects, including nonoxynonl-9, the acrosin inhibitor 4-acetamidophenyl 4-guanidinobenzoate, the polypeptide antibiotic derived from *Bacillus brevis*, gramicidin, and the polyphenolic aldehyde extracted from cottonseed, gossypol. Although these compounds are active against HIV-1, their spermicidal effects limit their use to situations in which conception is not desired. MAP30 and GAP31, however, are potent against HIV-1 and HSV, yet they lack spermicidal activity.

It has been documented that HIV-1 transmission can exist through artificial insemination with semen from infected donors. Thus, routine HIV-1 screening of all potential semen donors should be carried out before artificial insemination. Extracellular viral RNA and DNA were detected form semen samples form HIV-infected donors. It has been reported that treatment of infected semen samples by gradient centrifugation reduces extracellular viral DNA and RNA beyond detectable ranges, and thus lower the risk of HIV transmission.

Thus, treatment of semen with MAP30 and/or GAP31 alone or in combination with pre-washing before artificial insemination may further reduce the risk of viral transmission from infected donor to uninfected recipient. These non-spermicidal anti-HIV agents can be used for routine treatment of HIV-positive semen prior to in vitro fertilization. Also, for HIV-discordant couples desiring children, the use of non-spermicidal anti-HIV agents MAP30 or GAP31 may offer such couples addition hope of having healthy babies without infecting the babies' mothers.

In summary, it is shown here that endopeptidase digestion of MAP30 and GAP31 results in the generation of fragments with full antiviral and anti-tumor activity. These fragments are as active as their intact parent compounds, with $EC_{50}$s in the subnano-molar range. Thus, they may represent the biologically active forms of MAP30 and GAP31 in vivo. The fragments are sufficient for antiviral and anti-tumor activity whereas the additional C-terminal region is necessary for ribosome inactivation. The disparity of sequence and structural requirements for these activities indicates that ribosome inactivation is not prerequisite for the antiviral and anti-tumor effects.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Aron et al., "Inhibition of herpes simplex virus multiplication by the pokeweed antiviral protein" *Antimicrob Agents Chemother"*, 17:1032–3 (1980)

Bourinbaiar et al., "Acrosin inhibitor, 4'-acetamidophenyl 4-guanidinobenzoate, an experimental vaginal contraceptive with anti-HIV activity." *Contraception*, 51:319–322 (1995).

Bourinbaiar et al., "The activity of plant-derived antiretroviral proteins MAP30 and GAP31 against herpes simplex virus infection in vitro". *Biochem. biophys. Res. Commun.*, 219:923–929 (1996).

Chaddock et al., "Major structural differences between pokeweed antiviral protein and ricin A-chain do not account for their differing ribosome specificity" *Eur. J. Biochem.*, 233:159–66 (1996)

Cory et al., "Use of an aqueous soluble tetrazolium/formazan assay for cell growth assays in culture" *Cancer Commun*, 3:207–12 (1991)

Creighton, "Proteins: structure and molecule properties" W. H. Freeman & Co., San Francisco, pp. 79–86 (1983)

Day et al., "Structure and activity of an active site substitution of ricin A chain" *Biochemistry*, 35:11098–103 (1996)

Drapeau et al., "Purification and properties of an extracellular protease of *Ataphylococcus aureys" J. Biol. Chem.*, 247:6720–6 (1972)

Elliott et al., "Isolation and characterization of a lysine-specific protease from *Pseudomonas aeruginosa" J. Biol. Chem.*, 261:11258–65 (1986)

Huang et al., "Anti-HIV plant proteins catalyze topological changes of DNA into inactive forms" *Biofactors*, 4:37–41 (1992)

Husain et al., "Crystal structure of mormordin, a type I ribosome inactivating protein from the seeds of *Momordica charantia" FEBS Lett*, 342:154–8 (1994)

Laemmli, "Cleavage of structural proteins during the assembly of the head of beta-phi T4" *Nature*, 227:690–685 (1970)

Lee, C.-H., "In vitro spermicidal tests." *Contraception*, 54:131–147 (1996).

Lee-Huang et al., "A new inhibitor of HIV-1 infection and replication" *FEBS Letters*, 272:12–18 (1990)

Lee-Huang et al., "A new class of anti-HIV agents: GAP 31, DAP30 and DAP32" *FEBS Letters*, 291:139–144 (1991)

Lee-Huang et al., "Plant proteins with antiviral activity against human immunodeficiency virus, in Chu, C. K. and Cutler, H. G., eds." *Natural Products as Antiviral Agents* New York: Plenum, 153–170 (1992)

Lee Huang et al., "HIV-1 inhibition, DNA binding, RNA binding and ribosome inactivation activities in the N-terminal segments of the plant anti-HIV protein GAP31" *Proc. Natl. Acad. Sci. USA*, 91:12208–12212 (1994)

Lee-Huang et al., "Crystallization and Preliminary X-ray Analysis of GAP31: An Anti-HIV Protein" *J. Mol. Biol.*, 240:92–94 (1994)

Lee-Huang et al., "Inhibition of HIV-1 integrase by plant antiviral proteins MAP30 and GAP31" *Proc. Natl. Acad. Sci. USA*, 92:8818–8822 (1995)

Lee Huang et al., "Inhibition of human breast tumor MDA-MB-231 xenografts and HER2 Expression in SCID mice by anti-tumor agents MAP30 and GAP31" *Mol. Med*, (1999)

Lee-Huang et al., "Lysozyme and ribonucleases and anti-HIV components in beta-core preparations of hCG" *Proc. Natl. Acad. Sci. USA*", 96:2678–81 (1999)

Li et al., "Inhibition of the transcription of viral interleukin-1 (vIL-6) and viral cyclin D (vCD) genes in AIDS-related Kaposi's sarcoma cells by anti-HIV plant proteins MAP30"0 *J. AIDS and Human Retrovirology*, 17:A23 (1998)

Li et al., "Inhibition of caspase expression in AIDS-related Kaposi's sarcoma" XII*th* *International Conference on AIDS* (1998)

Mlsna et al., "Structure-of recombinant ricin A chain at 2.3 A" *Protein Sci.*, 2:429–35 (1993)

Montfort et al., "The three-dimensional structure of ricin at 2.8 A" *J. Biol. Chem.*, 262:5398–403

Monzingo et al., "The 2.5 A structure of pokeweed antiviral protein" *J. Mol. Biol.*, 233:705–15 (1993)

Rybak et al., "In vitro anti-tumor activity of the plant ribosome inactivating proteins MAP30 and GAP31" *Int. J. Onc.*, 5:1171–1176 (1994)

Tumer et al., "C-terminal deletion mutant of pokeweed antiviral protein inhibits viral infection but does not depurinate host ribosome" *Proc. Natl. Acad. Sci. USA*, 94:3866–71 (1997)

Wang et al., "Anti-HIV and anti-tumor protein MAP30, a 30 kDa single-strand type-1 RIP, shares similar secondary structure and beta-sheet topology with the A chain of ricin, a type-II RIP" *Protein Sci.* (1990)

Wong et al., "DNA polymerases alpha and delta are immunologially and structurally distinct" *J. Biol. Chem.*, 264:5924–28 (1989)

World Health Organization, *Laboratory Manual for the Examination of Human Semen and Sperm.* Cambridge University Press. Cambridge (1992).

Zarling et al., "Inhibition of HIV replication by pokeweed antiviral protein targeted to CD4+ cells by monoclonal antibodies" *Nature*, 347:92–5 (1990)

Zhou et al., "Structure of trichosanthin at 1.88 A resolution" *Proteins*, 19:4–13 (1994)

---

What is claimed is:

1. An isolated peptide or polypeptide having anti-tumor and anti-viral activity, wherein said peptide or polypeptide is selected from the group consisting of a truncated MAP30 protein, which lacks at least residues 1–11 and 233 to 263 of SEQ ID NO:1 and which truncated protein lacks the ribosomal inactivation activity of the MAP30 protein of SEQ ID NO:1.

2. The isolated peptide or polypeptide according to claim 1 which is a truncated MAP30 protein.

3. The isolated peptide or polypeptide according to claim 2, wherein said truncated MAP30 protein comprises residues 13 to 187 of SEQ ID NO: 1.

4. The isolated peptide or polypeptide according to claim 2, wherein said truncated MAP30 protein comprises residues 13 to 195 of SEQ ID NO: 1.

5. A composition comprising the isolated peptide or polypeptide of claim 1 and a pharmaceutically acceptable diluent, carrier, excipient or auxiliary agent.

* * * * *